United States Patent
Carney

(10) Patent No.: US 9,317,913 B2
(45) Date of Patent: Apr. 19, 2016

(54) METHOD FOR MEASURING THE ABSORPTION OF FLUID IN AN ABSORBENT PRODUCT

(75) Inventor: Joshua Carney, Mölndal (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 14/360,774

(22) PCT Filed: Dec. 21, 2011

(86) PCT No.: PCT/SE2011/051551
§ 371 (c)(1),
(2), (4) Date: May 27, 2014

(87) PCT Pub. No.: WO2013/095222
PCT Pub. Date: Jun. 27, 2013

(65) Prior Publication Data
US 2014/0301628 A1    Oct. 9, 2014

(51) Int. Cl.
*G06T 7/00* (2006.01)
*A61F 13/84* (2006.01)
*G06T 7/60* (2006.01)

(52) U.S. Cl.
CPC ............... *G06T 7/0002* (2013.01); *A61F 13/84* (2013.01); *G06T 7/602* (2013.01); *A61F 2013/8488* (2013.01); *A61F 2013/8491* (2013.01); *G06T 2207/10024* (2013.01); *G06T 2207/30124* (2013.01)

(58) Field of Classification Search
None
See application file for complete search history.

(56) References Cited

U.S. PATENT DOCUMENTS

| | | | |
|---|---|---|---|
| 4,834,733 | A | 5/1989 | Huntoon et al. |
| 5,144,284 | A | 9/1992 | Hammett |
| 5,416,469 | A | 5/1995 | Colling |
| 5,691,932 | A | 11/1997 | Reiner et al. |
| 5,978,712 | A | 11/1999 | Suda et al. |
| 6,266,557 | B1 | 7/2001 | Roe et al. |
| 6,354,991 | B1 | 3/2002 | Gross et al. |

(Continued)

FOREIGN PATENT DOCUMENTS

| | | |
|---|---|---|
| CN | 101472543 A | 7/2009 |
| CN | 102076298 A | 5/2011 |

(Continued)

OTHER PUBLICATIONS

The extended European Search Report issued on Mar. 4, 2015, by the European Patent Office in corresponding European Patent Application No. 11878058.4-1906. (4 pages).

(Continued)

*Primary Examiner* — David F Dunphy
(74) *Attorney, Agent, or Firm* — Buchanan Ingersoll & Rooney PC

(57) ABSTRACT

A method for measuring the absorption of fluid in an absorbent product includes at least the following steps performed by a mobile device having an image capturing device: capturing at least one image of a used absorbent product; determining a measure of absorption of fluid by the product based on image information in the captured image; and displaying information relating to the use of the absorbent product based the measure of absorption of fluid on the mobile device. The method can aid a user of absorbent product to choose the right type of product for the user's individual needs.

12 Claims, 2 Drawing Sheets

(56) References Cited

U.S. PATENT DOCUMENTS

| | | |
|---|---|---|
| 6,617,488 B1 | 9/2003 | Springer et al. |
| 6,652,449 B1 | 11/2003 | Gross et al. |
| 7,250,547 B1 | 7/2007 | Hofmeister et al. |
| 7,700,821 B2 | 4/2010 | Ales, III et al. |
| 7,737,322 B2 | 6/2010 | Ales, III et al. |
| 7,855,653 B2 | 12/2010 | Rondoni et al. |
| 7,977,529 B2 | 7/2011 | Bergman et al. |
| 8,121,691 B2 | 2/2012 | Gerber et al. |
| 8,395,014 B2* | 3/2013 | Helmer .................. A61F 13/42 340/573.5 |
| 2002/0026164 A1 | 2/2002 | Camarero Roy et al. |
| 2002/0145526 A1 | 10/2002 | Friedman et al. |
| 2003/0078553 A1 | 4/2003 | Wada et al. |
| 2004/0055367 A1 | 3/2004 | Swiecicki et al. |
| 2004/0078014 A1 | 4/2004 | Shapira |
| 2004/0100376 A1 | 5/2004 | Lye et al. |
| 2004/0220538 A1 | 11/2004 | Panopoulos |
| 2004/0230172 A1 | 11/2004 | Shapira |
| 2005/0033250 A1 | 2/2005 | Collette et al. |
| 2005/0137542 A1* | 6/2005 | Underhill ................ A61F 13/42 604/361 |
| 2005/0195085 A1 | 9/2005 | Cretu-Petra |
| 2005/0245839 A1 | 11/2005 | Stivoric et al. |
| 2006/0064037 A1 | 3/2006 | Shalon et al. |
| 2007/0142799 A1 | 6/2007 | Ales et al. |
| 2007/0252713 A1 | 11/2007 | Rondoni et al. |
| 2007/0252714 A1 | 11/2007 | Rondoni et al. |
| 2007/0255176 A1 | 11/2007 | Rondoni et al. |
| 2007/0270774 A1 | 11/2007 | Bergman et al. |
| 2008/0052030 A1 | 2/2008 | Olson et al. |
| 2008/0058740 A1 | 3/2008 | Sullivan et al. |
| 2008/0074274 A1 | 3/2008 | Hu et al. |
| 2008/0167535 A1 | 7/2008 | Stivoric et al. |
| 2008/0266117 A1 | 10/2008 | Song et al. |
| 2008/0300470 A1 | 12/2008 | Gerber et al. |
| 2008/0300651 A1 | 12/2008 | Gerber et al. |
| 2009/0062758 A1 | 3/2009 | Ales, III et al. |
| 2009/0326417 A1 | 12/2009 | Ales, III et al. |
| 2009/0326491 A1 | 12/2009 | Long et al. |
| 2010/0009713 A1 | 1/2010 | Freer |
| 2010/0076254 A1 | 3/2010 | Jimenez et al. |
| 2010/0098341 A1 | 4/2010 | Ju et al. |
| 2010/0168700 A1 | 7/2010 | Schmidt et al. |
| 2010/0201524 A1 | 8/2010 | Gallagher |
| 2011/0015496 A1 | 1/2011 | Sherman et al. |
| 2011/0046571 A1 | 2/2011 | Waldhorn |
| 2011/0063433 A1 | 3/2011 | Thonhauser |
| 2011/0125063 A1 | 5/2011 | Shalon et al. |
| 2011/0183712 A1 | 7/2011 | Eckstein et al. |
| 2011/0222774 A1 | 9/2011 | Hong et al. |
| 2011/0243425 A1* | 10/2011 | Maltbie et al. ................ 382/154 |
| 2011/0263952 A1 | 10/2011 | Bergman et al. |
| 2012/0035496 A1 | 2/2012 | Denison et al. |
| 2012/0040655 A1 | 2/2012 | Larkin |
| 2012/0157948 A1 | 6/2012 | Nhan et al. |
| 2012/0220969 A1* | 8/2012 | Jang ........................ A61F 13/42 604/361 |
| 2012/0256750 A1 | 10/2012 | Novak |
| 2012/0312086 A1 | 12/2012 | Paz et al. |
| 2013/0018231 A1 | 1/2013 | Hong et al. |
| 2013/0023786 A1 | 1/2013 | Mani et al. |
| 2013/0046239 A1 | 2/2013 | Gonnelli et al. |
| 2013/0110063 A1 | 5/2013 | Abraham et al. |
| 2013/0110064 A1 | 5/2013 | Richardson |
| 2013/0303867 A1 | 11/2013 | Elfstrom et al. |
| 2014/0292520 A1 | 10/2014 | Carney et al. |
| 2014/0327546 A1 | 11/2014 | Carney et al. |
| 2014/0333442 A1 | 11/2014 | Carney |

FOREIGN PATENT DOCUMENTS

| | | |
|---|---|---|
| DE | 103 26 489 A1 | 1/2005 |
| DE | 10 2006 053 405 A1 | 5/2008 |
| DE | 10 2009 054 097 A1 | 5/2011 |
| EP | 2 175 398 A1 | 4/2010 |
| JP | S62-299264 A | 12/1987 |
| JP | H10-234761 A | 9/1998 |
| JP | 2000-245779 A | 9/2000 |
| JP | 2000-333989 A | 12/2000 |
| JP | 2001-161732 A | 6/2001 |
| JP | 2001-314433 A | 11/2001 |
| JP | 2002-107361 A | 4/2002 |
| JP | 2002-113006 A | 4/2002 |
| JP | 2003-111797 A | 4/2003 |
| JP | 2003-126140 A | 5/2003 |
| JP | 2004-503014 A | 1/2004 |
| JP | 2004-212060 A | 7/2004 |
| JP | 2004-531287 A | 10/2004 |
| JP | 2005-087543 A | 4/2005 |
| JP | 2005-509934 A | 4/2005 |
| JP | 2007-167264 A | 7/2007 |
| JP | 2008-264232 A | 11/2008 |
| WO | WO 01/50996 A | 7/2001 |
| WO | 02/03902 A2 | 1/2002 |
| WO | 02/34127 A1 | 5/2002 |
| WO | 02/100292 A2 | 12/2002 |
| WO | 2007/128038 A1 | 11/2007 |
| WO | WO 2008/023289 A1 | 2/2008 |
| WO | WO 2008/038167 A2 | 4/2008 |
| WO | 2008/055991 A2 | 5/2008 |
| WO | WO 2008/147612 A | 12/2008 |
| WO | WO 2009/027871 A1 | 3/2009 |
| WO | WO 2010/040430 A1 | 4/2010 |
| WO | WO 2011/008838 A1 | 1/2011 |
| WO | WO 2011/054045 A1 | 5/2011 |
| WO | WO 2011/057723 A1 | 5/2011 |
| WO | WO 2011/080639 A1 | 7/2011 |
| WO | 2011/125003 A1 | 10/2011 |
| WO | WO 2011/126497 A1 | 10/2011 |
| WO | WO 2011/162402 A1 | 12/2011 |

OTHER PUBLICATIONS

Office Action (Notification of the First Office Action) issued on Jan. 6, 2015, by the State Intellectual Property Office (SIPO) of the People's Republic of China in Chinese Patent Application No. 201180075757.1, and an English Translation of the Office Action. (20 pages).

International Search Report (PCT/ISA/210) mailed on Sep. 18, 2012, by the Swedish Patent Office as the International Searching Authority for International Application No. PCT/SE2011/051551.

Notification of Transmittal of the International Preliminary Report on Patentability (Form PCT/IPEA/416) and International Preliminary Report on Patentability Chapter 11 of the Patent Cooperation Treaty (Form PCT/IPEA/409) dated Jun. 2, 2014, issued in corresponding International Application No. P41106658PCT00. (10 pgs).

U.S. Appl. No. 14/361,494, Carney, et al.
U.S. Appl. No. 14/362,261, Carney.
U.S. Appl. No. 14/363,313, Carney, et al.

Carney, Joshua, et al., U.S. Appl. No. 14/361,494 entitled "Method and Computer Program for Monitoring Use of an Abosrbent Product," filed in the U.S. Patent and Trademark Office on May 29, 2014.

Carney, Joshua, U.S. Appl. No. 14/362,261 entitled "Method, Monitoring System and Computer Program for Monitoring Use of an Absorbent Product," filed in the U.S. Patent and Trademark Office on Jun. 2, 2014.

Carney, Joshua, et al., U.S. Appl. No. 14/363,313 entitled "Method and Computer Program for Monitoring Use of an Abosrbent Product," filed in the U.S. Patent and Trademark Office on Jun. 6, 2014.

International Search Report (Form PCT/ISA/210) issued on Sep. 14, 2012, by the Swedish Patent Office in International Application No. PCT/SE2011/051565. (5 pages).

Notification of Transmittal of the International Preliminary Report on Patentability (Forms PCT/IPEA/416, PCT/IPEA/409 and PCT/Separate Sheet/409) issued on Feb. 20, 2014, by the European Patent Office in International Application No. PCT/SE2011/051565. (6 pages).

International Search Report (Form PCT/ISA/210) issued on Sep. 18, 2012, by the Swedish Patent Office in International Application No. PCT/SE2011/051558. (5 pages).

(56) References Cited

OTHER PUBLICATIONS

Notification of Transmittal of the International Preliminary Report on Patentability (Forms PCT/IPEA/409 and PCT/Separate Sheet/409) issued on Apr. 28, 2014, by the European Patent Office in International Application No. PCT/SE2011/051558. (6 pages).
Communication in cases for which no other form is applicable (Form PCT/IPEA/424) and Corrected International Preliminary Report on Patentability (Forms PCT/IPEA/409 and PCT/Separate Sheet/409) with Annex pages, issued on May 27, 2014, by the European Patent Office in International Application No. PCT/SE2011/051558. (13 pages).
International Search Report (Form PCT/ISA/210) issued on Sep. 18, 2012, by the Swedish Patent Office in International Application No. PCT/SE2011/051566. (5 pages).
Notification of Transmittal of the International Preliminary Report on Patentability (Forms PCT/IB/373) and the Written Opinion of the International Searching Authority (Form PCT/ISA/237) issued on Jun. 24, 2014, by the International Bureau of WIPO in International Application No. PCT/SE2011/051566. (8 pages).
The extended European Search Report issued on Oct. 14, 2014, by the European Patent Office in European Patent Application No. 11878154.1-1952. (9 pages).
Wai et al., "Smart Phone Reminder System for Managing Incontinence at Nursing Home," 2011 IEEE 15th International Symposium on Consumer Electronics (ISCE), (Jun. 14-17, 2011), pp. 254-259, Singapore.
U.S. Appl. No. 14/424,350, Carney, et al.
Office Action issued by the U.S. Patent and Trademark Office in the U.S. Appl. No. 14/363,313, mailed May 21, 2015, U.S. Patent and Trademark Office, Alexandria, VA. (33 pages).
Office Action issued by the U.S. Patent and Trademark Office in the U.S. Appl. No. 14/362,261, mailed May 12, 2015, U.S. Patent and Trademark Office, Alexandria, VA. (26 pages).
Office Action (Patent Examination Report No. 1) issued Apr. 17, 2015 by the Australian Intellectual Property Office in corresponding Australian Patent Application No. 2011383785, (3 pages).
Office Action issued by the U.S. Patent and Trademark Office in the U.S. Appl. No. 14/361,494, mailed Jun. 3, 2015, U.S. Patent and Trademark Office, Alexandria, VA (28 pages).
International Search Report (PCT/ISA/210) mailed on Jul. 4, 2013, by the Swedish Patent Office as the International Searching Authority for International Application No. PCT/SE2012/050910. (5 pages).
Written Opinion (PCT/ISA/237) mailed on Jul. 4, 2013, by the Swedish Patent Office as the International Searching Authority for International Application No. PCT/SE2012/050910. (9 pages).
Written Opinion of the International Preliminary Examining Authority (PCT/IPEA/408) mailed on Aug. 22, 2014, by the European Patent Office as the International Preliminary Examining Authority for International Application No. PCT/SE2012/050910. (7 pages).
International Preliminary Report on Patentability/Annex-Amended Sheets, issued in PCT/SE2012/050910. Jan. 28, 2015, European Patent Office, Berlin, DE (16 pages).
Carney, Joshua, et al., U.S. Appl. No. 14/424,350 entitled "Method and Mobile Applications using Cross-Sharing Database for Monitoring Use of Hygiene Products," filed in the U.S. Patent and Trademark Office on Feb. 26, 2015.
An English Translation of the Office Action (Notice of Reasons for Rejection) issued on Jul. 27, 2015, by the Japanese Patent Office in corresponding Japanese Patent Application No. 2014-548726. (4 pages).
An English Translation of the Office Action (Notice of Reasons for Rejection) issued on Aug. 10, 2015, by the Japanese Patent Office in Japanese Patent Application No. 2014-548727. (3 pages).
An English Translation of the Office Action (Notice of Reasons for Rejection) issued on Aug. 10, 2015, by the Japanese Patent Office in Japanese Patent Application No. 2014-548729. (5 pages).
An Examination Report issued on Oct. 23, 2015, by the Canadian Patent Office in corresponding Canadian Patent Application No. 2,857,627. (5 pages).
Final Office Action issued by the U.S. Patent and Trademark Office in U.S. Appl. No. 14/363,313, mailed Nov. 5, 2015, U.S. Patent and Trademark Office, Alexandria, VA. (26 pages).
Final Office Action issued by the U.S. Patent and Trademark Office in U.S. Appl. No. 14/362,261, mailed Nov. 13, 2015, U.S. Patent and Trademark Office, Alexandria, VA. (24 pages).

* cited by examiner

METHOD FOR MEASURING THE ABSORPTION OF FLUID IN AN ABSORBENT PRODUCT

TECHNICAL FIELD

The present disclosure relates to a method for measuring the absorption of fluid in an absorbent product.

BACKGROUND

Today, it is common for both children and adults to use various types of absorbent hygiene products such as diapers, incontinence pads, sanitary napkins etc.

In particular, with regard to products such as incontinence pads, there is a need for a user of such a product to wear a type of product which is adapted for the user's individual needs. This means that the incontinence pad which is to be used should have a sufficient and suitable absorption capacity as regards fluid.

Users of incontinence products may sometimes have difficulty in selecting the correct type of product on the market of incontinence products, i.e. selecting the product which is best suited for the user's individual needs. This is emphasized by the fact that users of incontinence products are often elderly or disabled persons. For this reason, there is a need for methods and devices to aid such users in finding and using the correct product adapted for their own needs.

A known solution to the above-mentioned problem is to use available product information from manufacturers of absorbent products to find guidance towards a product which is suitable with regard to a user's individual needs. However, as indicated above, it has been found that many users of in particular incontinence pads may find it difficult to get an overview of the products available on the market and to choose the most appropriate product for each person's individual needs.

SUMMARY

Consequently, it is an object of the present disclosure to solve the above-mentioned problem and to provide a method and device which can be used to assist the user of an absorbent product in order to find a suitable product which can be regarded as suitable based on the user's individual needs.

In particular, it is an object of the present disclosure to provide a method and device which is easy to use and which gives straight-forward and clear information regarding suitable products to use.

Yet another object of the present disclosure is to provide a method that facilitates, for caregivers of persons suffering from incontinence, in finding a suitable absorbent product to use.

These and other objects are achieved by a method for measuring the absorption of fluid in an absorbent product, comprising certain steps which are performed by a mobile device comprising an image capturing device. More precisely, the method comprises the following steps: capturing at least one image of a used absorbent product; determining a measure of absorption of fluid by said product based on image information in the captured image; and displaying information relating to the use of the absorbent product based on said measure of absorption of fluid on said mobile device.

The present disclosure relies on the insight that a mobile device, provided with an image capturing device such as a conventional camera provided on a mobile device, for example a mobile phone, can be used to scan or swipe along a used absorbent product and to capture an image (or a sequence of images) containing image information which can be used, together with suitable software, to generate information related to the use of said product based on image information in the captured image.

Due to the fact that a mobile phone can be used to present information related to the use of the product, the user may obtain such information in order to be guided in selecting the correct product to be used based on the user's degree of incontinence.

The information being displayed based on the measure of absorption of fluid by the absorbent product may be any information related to the use of the absorbent product. Preferably, the information comprises a recommendation to the user of said absorbent product regarding a suitable absorbent product to use. For example, the information may comprise a recommendation to exchange the currently used absorbent product for another type of absorbent product having a higher or lower capacity to absorb fluid. Such information can be displayed on the mobile device itself, or on a communication device to which the mobile device is communicatively connectable, e.g. a mobile device of the caregiver.

That the information is displayed based on the measure of absorption of fluid by the absorbent product means that the content of the information and additionally also the way the information is displayed to the user is selected by the mobile device based on the measure of absorption of fluid.

The use of a mobile device comprising an image capturing device, such as a mobile phone, a personal digital assistant (PDA), a tablet computer or any other hand-held computing device makes the method readily available to anyone in possession of such a mobile device. The method is performed by the mobile device through execution of a computer program, which, in a preferred embodiment, is realised in form of an App. The App is suitably arranged to be downloadable to a storage medium of the mobile device.

By allowing the method to be performed through execution of an App that may be downloaded into existing mobile devices, the method truly becomes readily available to any user.

In order to perform the method, the mobile device is suitably placed in a position where it is capable of capturing one or more images of the used absorbent product. Preferably, the image capturing device is a camera which is sensitive enough to register images of relatively high resolution. In particular, the image quality and resolution of the image capturing device is suitably sufficient for the software to decide which parts of the used absorbent product have absorbed fluid and which parts have not. The results of the image capturing step is more reliable if a high-resolution camera is used and also if the mobile device is held steadily at a suitable distance from the used absorbent product.

Moreover, the method may involve the step of obtaining capacity information relating to the absorbent product's capacity to absorb fluid, and to select the information that is to be displayed on the mobile device based on both the measure of absorption and said capacity information. The capacity information may be any information that can be used to derive information about the product's capacity to absorb fluid. It should be understood that there are many measures of the product's absorption capacity, including but not limited to its capacity to absorb a maximum total volume of fluid, its capacity to absorb a maximum volume of fluid per unit area, and its capacity to absorb fluid in different parts of the product. The capacity information may be obtained either by manual input of information from the user or from automatic retrieval of information from a product database. The capacity information may comprise information related to the type of the absorbent product, the absorbency level of the absorbent product, and/or the size of the absorbent product.

In one embodiment, the capacity information is used to compare the capacity of the absorbent product with an estimated amount of fluid absorbed by the used product, which amount may be estimated based on the determined measure of absorption of fluid by the product. The information displayed on the mobile device may then be selected based on said comparison.

In summary, this means that well-founded and easily understandable information regarding suitable products to use can be provided to the user via the mobile device's graphical interface. In particular, the present disclosure can be used to instruct or recommend the user to exchange his or her current product for another product which is more suitable with regard to the user's individual incontinence situation.

Furthermore, the present disclosure suitably makes use of a light source which for this purpose in integrated within the mobile device. Such is the case of conventional mobile phones, which use a light source used for photographing where natural light conditions are insufficient. Consequently, the method suitably comprises a step of illuminating the used absorbent product in question with an integrated light source of the mobile device during the image capturing stage.

Alternatively, the present disclosure could be used for capturing images with the aid of a separate light source, i.e. it does not have to be an integrated part of the mobile device.

The image capturing can be carried out in at least two ways; the image capturing device can be used either for capturing one single image of the entire used absorbent product; or the image capturing device can be used for obtaining a video or a multiple-image sequence of images while scanning, or swiping, the mobile device along the longitudinal (or transversal) direction of the used absorbent product. Both these types of methods enable the user to input image information into the software of the mobile device in order to allow a processor of the mobile device to determine to what extent the absorbent product has been used, e.g. by determining the percentage of the total area of the product that is wet.

As indicated above, the method may be a computer-implemented method performed by a mobile device through execution of a computer program. Thus, according to another aspect of the present disclosure there is provided a computer program for measuring the absorption of fluid in an absorbent product. When executed by a microprocessor, the computer program is configured to perform a method for measuring the absorption of fluid in an absorbent product as describe above.

The present disclosure also provides a computer program product comprising a non-volatile memory for storing computer-readable instructions, wherein the above mentioned computer program is encoded on said non-volatile memory.

Furthermore, the present disclosure provides a mobile device for measuring the absorption of fluid in an absorbent product. The mobile device comprises an image capturing device, a processor and a storage medium for storing computer programs executable by said processor. Also, the storage medium stores the above mentioned computer program.

The absorbent product as mentioned above can be any form of absorbent personal hygiene article, such as a male or female incontinence protector, a sanitary pad, a panty liner or a diaper, for example a diaper with tape fastener, a pant diaper or a belted diaper.

DETAILED DESCRIPTION

Figure 1:
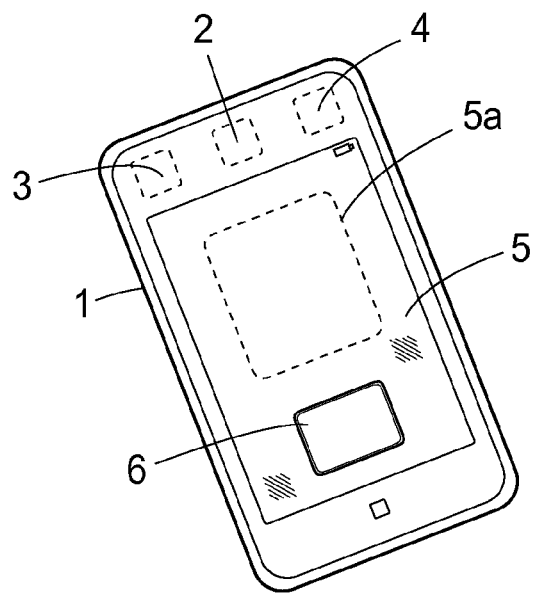
FIG. 1 illustrates a mobile device operable to perform a method according to the present disclosure through execution of a computer program.

FIG. 1 illustrates a mobile device 1 for performing the method according to the present disclosure. The mobile device 1 in FIG. 1 is a mobile phone in form of what is often referred to as a smartphone but it should be appreciated that the mobile device according to the present disclosure may be any type of hand-held computing device, such as a personal digital assistant (PDA) or a tablet computer, devised and configured as set forth below.

The mobile device 1 comprises an integrated image capturing device 2 for capturing images and video recordings, to be subsequently stored in the mobile device 1. Such image capturing devices 2 are generally known and typically comprise an image sensor and a lens (not shown) which are used for example in mobile phones for capturing photographic images.

Furthermore, the mobile device 1 comprises a processor 3 for processing data. The data may be received from communication devices to which the mobile device 1 is communicatively connectable via a network, or stored on a digital storage medium 4 of the mobile device, which storage medium is accessible by the processor 3.

The mobile device 1 is further seen to comprise a display 5 for displaying information to a user, and, if realised in form of a touch-display, also for receiving information from the user in form of user input. The mobile device 1 may also comprise other means for receiving user input, such as buttons, microphones, as well as means for outputting signals and information, such as for example a loudspeaker etc. Such additional devices are generally known and for this reason they are not explained in detail here.

The mobile device 1 is operable to perform all method steps of the inventive method, which method steps will be described in more detail below, through execution of a computer program stored in the storage medium 4.

Preferably, the computer program is realised in form of a stand-alone application, meaning that no data has to be received from external devices in order to run the program. However, the computer program may also be a client application of a distributed software solution further comprising a server-side application residing in an application server to which the mobile device is communicatively connectable. In this case, some of the method steps described below may be performed by the application server through execution of the server-side application.

In a preferred embodiment of the present disclosure, the computer program stored on the mobile device 1 is realised in form of an App. An App, sometimes referred to as a mobile app or a mobile application, is a software application specifically designed to run on mobile devices such as smartphones and tablet computers. The App is downloadable into the storage medium 4 from a download server to which the mobile device 1 is connectable. The App may be adapted to a particular mobile operating system, such as Apple iOS, Google Android or Blackberry OS and distributed through known application distribution platforms.

It should thus be appreciated that "the App" hereinafter refers to a computer program stored on the storage medium 3 of the mobile device 1. As indicated in a simplified form in FIG. 1, the App can be executed by means of a particular icon 6 on which the user touches.

Figure 2:
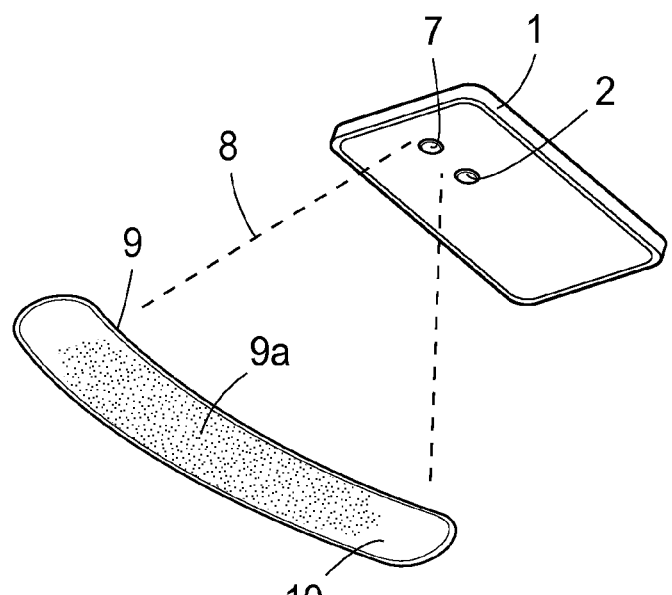
FIG. 2 illustrates said mobile device from another angle as compared with FIG. 1 and showing the method according to the present disclosure during image capturing.

FIG. 2 is a further view, from an angle as seen from below of the mobile device 1, in which the image capturing device 2 is also shown. Preferably, the image capturing device 2 is in the form of a camera and is positioned on the rear side of the mobile device 1. However, the present disclosure is not limited to such placement only, i.e. the image capturing device 2 could for example be placed on the top surface or along the side edge of the mobile device 1.

Furthermore, the mobile device 1 preferably comprises a light source 7 which can be a conventional flash-type light device as used in many of today's mobile devices such as mobile phones. The light source 7 is arranged for generating a field of light 8 directed from the mobile device 1. Alternatively, the device could be used with a separate light source or with natural ambient light only, if the light conditions are sufficient.

As shown in FIG. 2, the mobile device 1 is used in connection with an absorbent product 9, suitably in the form of an incontinence pad. It should be noted that the method according to the present disclosure is carried out using a used absorbent product 9. For this reason, a certain part of the product 9 which has been filled with fluid such as urine is generally indicated by means of reference numeral 9a.

Generally, the present disclosure is arranged for being used with all types of absorbent products such as male or female incontinence pad, a sanitary pad or a diaper, for example a diaper with tape fastener, a pant diaper or a belted diaper.

The view in FIG. 2 of the absorbent product 9 is from below, i.e. it is the back side 10 of the absorbent product 9 that is illustrated in FIG. 2.

Figure 3A:
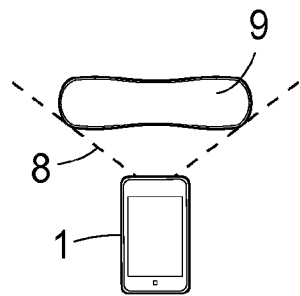
FIGS. 3a and 3b show, in a general manner, two methods by means of which the present disclosure can be implemented.
Figure 3B:
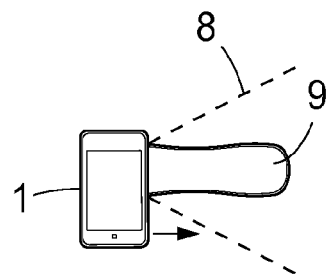

FIGS. 3a and 3b show two different ways of operating the mobile device 1 in connection with the present disclosure. Firstly, in FIG. 3a there is shown an arrangement which generally corresponds to FIG. 2, i.e. an arrangement in which the mobile device 1 is held by the user, with the light source being switched on so as to provide a field of light 8 directed towards the absorbent product 9. The user generates the capturing of an image, for example by touching a corresponding icon (not shown) on the display. This image is then stored in the digital storage medium 4 (cf. FIG. 1) for subsequent processing by means of the microprocessor 3. This will be described in more detail below.

FIG. 3b shows how the mobile device 1 is used for scanning (or "swiping") along the absorbent product, as indicated by means of an arrow. In this case, the image capturing device 2 of the mobile device 1 is used for capturing a number of images or for capturing a video sequence. The purpose with this is also to store image-related information in the digital storage medium 4 (cf. FIG. 1) for subsequent processing by means of the microprocessor 3.

Figure 4:
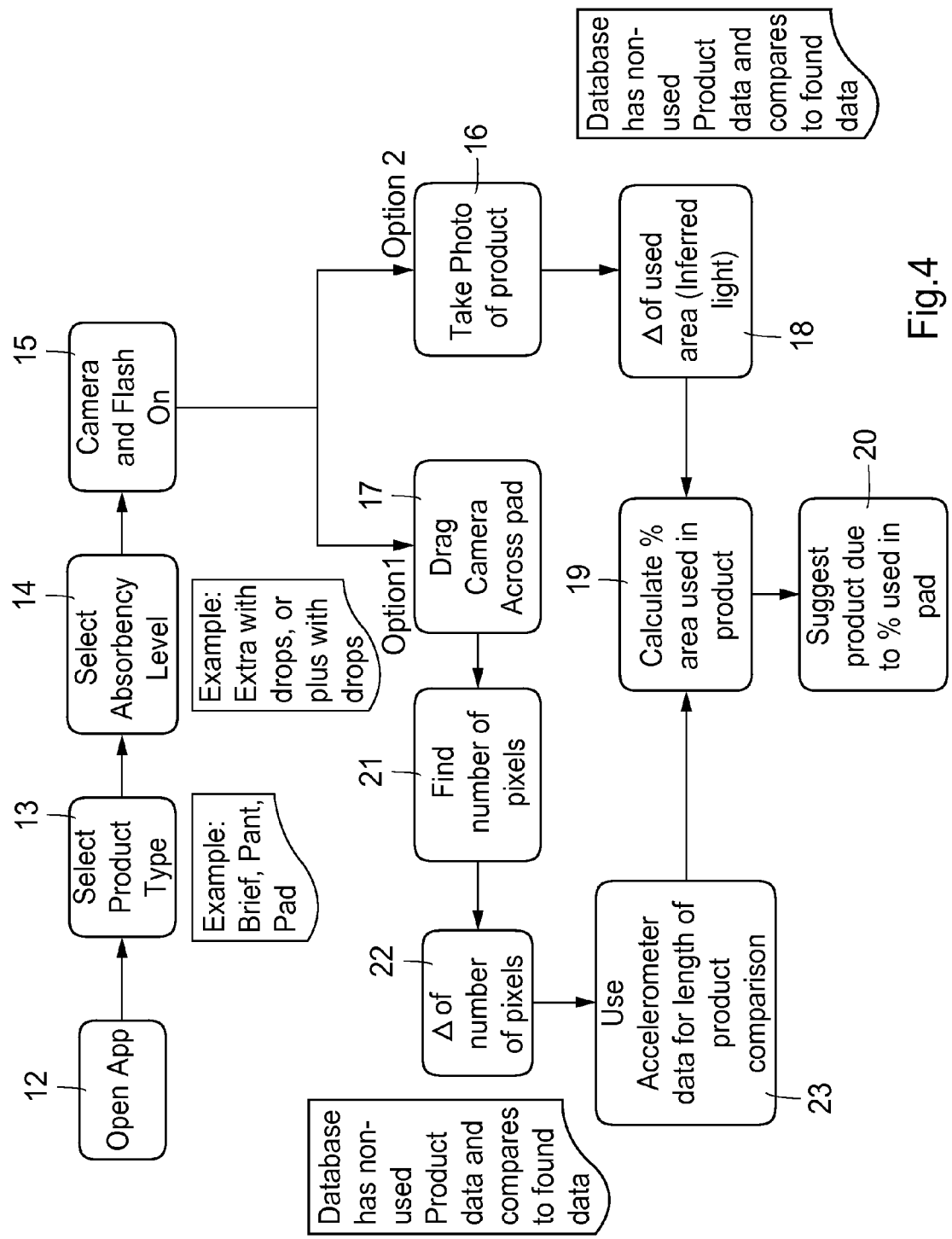
FIG. 4 is a flow chart illustrating an embodiment of the method according to the present disclosure.

A suitable method for measuring the absorption of fluid according to the present disclosure will now be described in greater detail. With reference to FIG. 4, a sequence of steps for carrying out said method will now be described.

Firstly, in a first step, the user initiates the process, suitably by touching an icon such as a "start" icon 6 on the mobile device's 1 display 5, as shown in FIG. 1. This is also indicated by means of reference numeral 12 in FIG. 4.

Suitably, the user can also provide additional information regarding for example which type of product the user wishes to investigate (reference numeral 13). Preferably, the user can also enter information relating to a level of absorbency of the absorbent product (reference numeral 14).

The steps 13 and 14 can be combined into a general step of obtaining capacity information relating to the absorbent product's capacity to absorb fluid. This step may comprise a first step of obtaining information about the type of the absorbent product, i.e. information telling the App whether the absorbent product is an incontinence pad, a diaper, etc. To this end, the App is preferably configured to display a list of several product types on the display of the mobile device 1, and to obtain the product type information by having the user indicating the correct alternative in the list of product types. It may further comprise a second step in which the App obtains information about the absorbency level of the absorbent product. Many types of absorbent products, e.g. incontinence pads, are available within a wide range of absorbency levels, and the product's capability to absorb and retain liquid and/or faeces may vary substantially between different absorbency levels. Typically, the absorbency level is the level of the product's absorption capacity on a predefined scale, which level and scale are indicated on the package of the absorbent product. Preferably, the App is configured to display a scale of absorbency levels corresponding to a scale of absorbency levels presented on the package of the absorbency product, and to obtain the absorbency level by having the user indicating the correct absorbency level on the displayed scale.

In other embodiments, the App may be configured to obtain the capacity information automatically through automatic identification of the absorbent product. The App may be configured to identify the product automatically by means of the image capturing device 2 and suitable image recognition software, an RFID reader or a barcode scanner of the mobile device 1, and to obtain the capacity information automatically from a product database stored locally on the mobile device 1 or a product database stored on an application server to which the mobile device 1 is connectable. To this end, the absorbent product may be provided with means for facilitating automatic identification thereof, such as a barcode (e.g. a QR code) or an RFID tag.

Before capturing the image or images of the used absorbent product, the user should preferably switch on the light source (reference numeral 15) on the mobile device 1, i.e. the light source referred to by reference numeral 7 in FIG. 2.

The next phase is the capturing of image-related information. The user then has two options, i.e. capturing a single picture by means of the image capturing device 2 (see reference numeral 16) or scanning the mobile device 1 along the absorbent product 9 (reference numeral 17). The option of taking a single photo is first described. The user directs the mobile device 1 towards the absorbent product 9 and touches a corresponding icon on the display in order to activate the image capturing device 2. Image data regarding the captured image may then be stored in the digital storage medium 4 (cf. FIG. 1) for subsequent processing by the processor 3 of the mobile device 1. Alternatively, the image data may be processed in real time without saving the captured image. The storage medium 4 may also be provided with data regarding a corresponding non-used product. This allows a comparison to be made between image data of the used product and data representing a corresponding non-used product. Thereby, information regarding the absorption of fluid by the used product can be derived.

The image processing of the at least one captured image may involve analysis of colour or light intensity information of the pixels of the captured image. However, the image may be analysed with respect to any parameter which can be used to distinguish parts of the product 9 in which liquid is absorbed from other parts of the product 9 in which no liquid is absorbed. A colour and/or light intensity analysis will reveal that the areas 9a of the product 9 which have absorbed liquid, such as urine, will present a different colour and/or a different light intensity than the remaining, "dry", areas of the product 9. In this manner, the processor 3 can be arranged to determine the magnitude of the area 9a and/or the percentage of the area of the entire product covered by the wet are 9a.

In summary, and in accordance with the principles of the present disclosure, the processor 3 is arranged to detect the magnitude of the "used" area 9a (cf. FIG. 2) of the absorbent product 9, i.e. the magnitude of the area 9a that has absorbed liquid to an extent that is detectable by analysing the colour, the light intensity, or any other parameter indicative of liquid absorption, in the captured image. This is carried out by analysing the pixel information in the image that has been captured by the image capturing device 2. The processor 3 can then determine for example the percentage of the product 9 that is filled with fluid (reference numeral 18).

According to a suitable embodiment, the display 5 of the mobile device 1 can be arranged so that it shows a frame 5a, the intention of which is to indicate to the user that the image capturing device 2 should be pointed towards the absorbent product 9 so that the product 9 is seen inside the frame 5. In this manner, the image of the product 9 is captured in a similar manner each time the method is used.

The processor 3 can be used for determining a measure of absorption of fluid by the product based on a comparison between image data in the captured image and pre-stored data related to the above-mentioned non-used absorbent product of the type currently used. In other words, the magnitude of the area filled with fluid can be divided with the magnitude of the total, "non-filled", area of the product, thereby allowing a calculating of the percentage of the whole absorbent product which is filled with liquid (reference numeral 19). It should, however, be appreciated that the percentage of the product that is used may also be calculated based on the captured image data alone, without comparison with image data relating to non-used products of the same type. For example, the pixels of the captured image can be divided into two groups based on the colour or light intensity of each pixel, wherein one group comprises pixels depicting dry areas of the product 9 and the other group comprises pixels depicting wet areas of the product 9. By comparing the number of pixels in each group, or in other ways estimating the areas of the captured image covered by pixels from the respective group, the percentage of the product that is "used" can be determined from the captured image data alone.

As a next step, the processor 3 can provide information regarding suitable products for the user to use, based on the measure of absorption of fluid as calculated by the processor 3 (reference numeral 20). For example, if less than a predetermined threshold value, for example 50%, of the absorbent product 9 is filled with liquid, it can be determined that the user has used an absorbent product which is over-dimensioned, i.e. too large. On the other hand, if more than another predetermined threshold value, for example 95%, of the absorbent product 9 is filled with liquid, it can be determined that the user has used an absorbent product which is under-dimensioned, i.e. too small.

For this reason, the processor 3 is arranged to propose to the user a product which is the most suitable for this particular user. More precisely, the processor 3 may compare the actual amount of fluid absorbed by the absorbent product 9 with corresponding data related to a number of alternative absorbent products having been stored beforehand in the digital storage memory 4. A suitable suggestion for an absorbent product, having properties and absorbent capacity being the most suitable for the user, is then presented via the display 5 of the mobile device 1.

Obviously, the processor 3 may be adapted for displaying a variety of information on the display 5. For example, detailed data related to the actual absorbed amount of fluid in the used absorbent product can be displayed. Also, data related to a comparison between the actual absorbed amount of liquid and the capacity of a non-used absorbent product of the same type as the one being used can also be displayed. For the normal user, however, it can be assumed that the most helpful information to be displayed is information directly related to suggestions on products to be used by the user in question. In this manner, the present disclosure can be used in a highly user-friendly manner in order to help for example people suffering from incontinence to use the most effective and appropriate incontinence pads.

As shown in FIG. 4, as indicated by reference numeral 17, the user may alternatively use the mobile device 1 in a manner so as to scan it along the used absorbent product (cf. FIG. 3b). During this process, the processor 3 is used together with the image capturing device 2 so as to determine the magnitude of the area of the absorbent product 9 which is filled with liquid, i.e. to measure the level of absorption of fluid in the absorbent product 9. According to this alternative method, the mobile device 2 is scanned along the product 9 so that a number of images are captured or so that a video sequence is captured. Any of these methods are used in order to capture a number of pixels of image information along the length of the product 9 (reference numeral 21). In a subsequent step (reference numeral 22), the processor 3 is arranged for determining how large part of the absorbent product 9 is filled with liquid, i.e. how many pixels as compared with the total number of pixels in the product 9 which correspond to liquid being absorbed. This is carried out by analyzing the captured pixels with regard to colour, light intensity or any other parameter which can be used to distinguish parts of the product 9 in which liquid is absorbed from other parts of the product 9 in which no liquid is absorbed.

Also, the mobile device 1 may use a built-in accelerometer (not shown) which senses the orientation of the mobile device 1. The processor 3 may then determine the length of the absorbent product 9 based on data from the accelerometer (reference numeral 23).

In this manner, the processor 3 may also measure the absorption of fluid in the used absorbent product 9 based on a calculation of the part of the product's area in which fluid is absorbed (reference numeral 19).

The present disclosure is not limited to the embodiments described above, but can be varied within the scope of the subsequent claims.

The invention claimed is:

1. A method for measuring absorption of fluid in an absorbent product, comprising at least the following steps, performed by a mobile device comprising an image capturing device:
   obtaining capacity information relating to an absorption capacity of the absorbent product prior to use by automatic retrieval of information from a product database;
   capturing at least one image of the absorbent product after it has been used;
   determining a measure of absorption of fluid by said used absorbent product based on image information in the captured image;
   estimating, from said measure of absorption of fluid, an estimated amount of fluid absorbed by said used absorbent product, comparing the estimated amount of absorbed fluid with the obtained absorption capacity of said absorbent product, and displaying information relating to the use of the used absorbent product based on said measure of absorption of fluid on said mobile device, wherein said information is based on said comparison.

2. The method according to claim 1, wherein the information displayed comprises a recommendation to the user of said used absorbent product regarding a suitable absorbent product to use.

3. The method according to claim 1, wherein the obtained capacity information is obtained from a user of the mobile device in form of user input.

4. The method according to claim 1, wherein the step of obtaining capacity information comprises a step of automatically identifying said absorbent product in the field of view of the image capturing device, and obtaining the capacity information automatically from the product database.

5. The method according to claim 1, further comprising the step of illuminating the used absorbent product with an integrated light source of the mobile device during capturing of said at least one image.

6. The method according to claim 1, wherein the at least one image is a plurality of close-up images capturing different parts of the used absorbent product.

7. The method according to claim 1, wherein the at least one image is a plurality of images forming a video sequence captured by scanning the used absorbent product with the mobile device.

8. The method according to claim 1, wherein the method is performed on one or more real-time images of the used absorbent product.

9. The method according to claim 1, wherein the absorbent product is an absorbent personal hygiene article.

10. The method according to claim 9, wherein the absorbent personal hygiene article is one of a male or female incontinence protector, a sanitary pad, a diaper with tape fastener, a pant diaper and a belted diaper.

11. A non-transitory computer readable recording medium storing thereon a program for measuring the absorption of fluid in a used absorbent product, wherein the computer program, when executed by a processor of a mobile device comprising an image capturing device, causes the mobile device to perform the method according to claim 1.

12. A mobile device that measures absorption of fluid in a used absorbent product, the mobile device comprising an image capturing device, a processor, and a computer readable recording medium storing the computer program according to claim 11.

\* \* \* \* \*